(12) United States Patent
Gao

(10) Patent No.: US 12,390,364 B2
(45) Date of Patent: Aug. 19, 2025

(54) FOLDING PRESSING-TYPE BALLOON STRUCTURE

(71) Applicant: GUANGZHOU VESBER BIOTECHNOLOGY CO., LTD., Guangzhou (CN)

(72) Inventor: Qianying Gao, Guangzhou (CN)

(73) Assignee: GUANGZHOU VESBER BIOTECHNOLOGY CO., LTD., Guangzhou (CN)

( * ) Notice: Subject to any disclaimer, the term of this patent is extended or adjusted under 35 U.S.C. 154(b) by 405 days.

(21) Appl. No.: 17/778,464

(22) PCT Filed: Apr. 30, 2020

(86) PCT No.: PCT/CN2020/088430
§ 371 (c)(1),
(2) Date: May 20, 2022

(87) PCT Pub. No.: WO2021/098155
PCT Pub. Date: May 27, 2021

(65) Prior Publication Data
US 2023/0000678 A1  Jan. 5, 2023

(30) Foreign Application Priority Data
Nov. 21, 2019 (CN) .......................... 201911148108.4

(51) Int. Cl.
*A61F 9/007* (2006.01)
(52) U.S. Cl.
CPC .. *A61F 9/00727* (2013.01); *A61F 2210/0004* (2013.01); *A61F 2210/0061* (2013.01)
(58) Field of Classification Search
CPC .......... A61F 9/00727; A61F 2210/0004; A61F 2210/0061; A61F 9/007; A61F 2/14;
(Continued)

(56) References Cited

U.S. PATENT DOCUMENTS 3,435,826 A * 4/1969 Fogarty ................. A61M 25/10
606/192
4,299,227 A * 11/1981 Lincoff ................. A61M 29/02
606/107
(Continued)

FOREIGN PATENT DOCUMENTS

CN  2647270 Y  10/2004
CN  201019909 Y  2/2008
(Continued)

OTHER PUBLICATIONS

Extended European Search Report for European Counterpart Application No. 20891122.2 mailed Apr. 14, 2023 (7 pages).
(Continued)

*Primary Examiner* — Shaun L David
*Assistant Examiner* — Rachael L Geiger
(74) *Attorney, Agent, or Firm* — Andrew C. Cheng

(57) ABSTRACT

A foldable pressing-type balloon structure (10), comprising a balloon body (100) used for arrangement in the Tenon capsule and a drainage component (200) capable of being closed automatically. The balloon body (100) is formed with a balloon cavity used for supplying normal saline or air; the balloon body (100) has a planar first surface (110) and a curved second surface (120); the height of the balloon body (100) along the first surface (110) is 0.2-2.0 cm; the drainage component (200) is connected to the second surface (120) of the balloon body (100) and communicated with the balloon cavity. The foldable pressing-type balloon structure (10) is implanted under the Tenon capsule, and a break is sealed by pressing by filling the inside of the balloon body (100) with a medium. Compared with scleral buckles in the prior art, fixing with buckles is not required, and it is only necessary to fix the position of the drainage component (200) by suturing to prevent displacement, so that an incision in surgery is reduced; moreover, because fixing with buckles is (Continued)

not required, extraocular muscles will not be pulled, so that a patient does not feel uncomfortable after surgery. The surgical method is simple in operation, the difficulty is reduced, and the time required for surgery is shortened.

12 Claims, 4 Drawing Sheets

(58) Field of Classification Search
CPC .......... A61F 2/141; A61F 2/142; A61F 2/145; A61F 2/1451; A61F 2/1453; A61F 2/147; A61F 2/148; A61F 2/15; A61F 2/1694; A61F 9/0008; A61F 9/0017; A61F 9/0026
See application file for complete search history.

(56) References Cited

U.S. PATENT DOCUMENTS

| | | | |
|---|---|---|---|
| 5,286,261 | A | 2/1994 | Roizenblatt |
| 5,330,529 | A * | 7/1994 | Cepela .................... A61F 2/141 |
| | | | 623/6.64 |
| 2010/0286773 | A1 | 11/2010 | Gao |
| 2010/0305694 | A1 | 12/2010 | Lee et al. |
| 2018/0049918 | A1 | 2/2018 | Benner et al. |
| 2018/0185288 | A1 | 7/2018 | Schachar et al. |

FOREIGN PATENT DOCUMENTS

| | | |
|---|---|---|
| CN | 109692072 A | 4/2019 |
| CN | 110037853 A | 7/2019 |
| CN | 110859702 A | 3/2020 |
| JP | 2003521336 A | 7/2003 |
| JP | 2011515248 A | 5/2011 |
| WO | 92/03996 A1 | 3/1992 |
| WO | 0156510 A1 | 8/2001 |

OTHER PUBLICATIONS

Japanese Office Action, and English translation thereof, for Japanese Counterpart Application No. 2022-529825 mailed Jun. 6, 2023 (10 pages).

VESBER Fcvb & FCB appeared in the European retina conference, and experts at home and abroad gathered to discuss new technologies, Sep. 11, 2019, retrieved from 'https://vesber.com/fcvb-fcb-appeared-in-the-european-retina-conference-and-experts-at-home-and-abroad-gathered-to-discuss-new-technologies/,' (11 pages). (Searching date was May 25, 2023, according to Office Action for Japanese Application No. 2022-529825).

VESBER Fcvb & FCB show up at the grand event, and the booth of vesber is wonderful, Sep. 9, 2019, retrieved from 'https://vesber.com/coss2019,' (5 pages). (Searching date was May 25, 2023, according to Office Action for Japanese Application No. 2022-529825).

International Search Report and Written Opinion, and English Translation of the Search Report thereof, for International Application No. PCT/CN2020/088430, mailed Aug. 19, 2020 (14 pages).

Chinese First Office Action, and English Translation thereof, for priority Chinese Application No. 201911148108.4, mailed Nov. 4, 2020 (13 pages).

Chinese Second Office Action, and English Translation thereof, for priority Chinese Application No. 201911148108.4, mailed Jul. 14, 2021 (13 pages).

Indian Office Action, and English Translation thereof, for Indian Counterpart Application No. 202247029208, mailed Sep. 19, 2022 (5 pages).

* cited by examiner

FOLDING PRESSING-TYPE BALLOON STRUCTURE

CROSS-REFERENCE TO RELATED APPLICATIONS

This application is a national stage for International Application PCT/CN2020/088430, filed on Apr. 30, 2020, which claims priority from Chinese Patent Application No. 201911148108.4 filed on Nov. 21, 2019, the entire content of which is incorporated herein by reference.

TECHNICAL FIELD

The present disclosure relates to the field of vision rehab, in particular to a foldable pressing balloon structure.

BACKGROUND

Retinal detachment is a disease that seriously affects vision and may be classified into rhegmatogenous retinal detachment, exudative retinal detachment and traction retinal detachment. Once retinal detachment lesions reaches the macula, it may directly affect the patient's vision and even cause blindness. At present, the conventional methods for clinical treatment of retinal detachment are scleral buckling surgery and vitrectomy. For a fresh, single hole with a well-defined position, scleral buckling may be selected. During the surgery, the position of the hole is accurately positioned, and a silicone pad is fixed with a encircling band on the eyeball wall to press inward and seal the hole, thereby achieving a therapeutic effect. This method cause relatively less damage to the eyeball. For a patient with a plurality of holes in different body parts at the same time, the treatment from the inside with vitrectomy is required to close the plurality of holes. However, the vitrectomy is very harmful to the inside of the eyeball, and the eyeball needs to be filled with media after surgery until it heals. Besides, these two methods are different choices corresponding to the severity of the patient's condition. If the scleral buckling surgery fails to cure the patient successfully, the vitrectomy may be an option to cure the patient, but the surgery result of vitrectomy is not capable of being reversed.

In the prior art, a patent with an publication number US 2010305694 A1 describes a scleral encircling band, the design of which focuses on solving the problem of suturing a plurality of body parts during the surgery, but the treatment idea does not break through the concept of encircling band, but the surgical method is more optimized, such that the defects of encircling band surgery is not solved. A patent with a publication US 2018185288 A1 describes a substance and a device for injecting the substance into the vitreous cavity of eyeball. The substance can slow down the flow rate of the fluid in the vitreous cavity, increase the viscosity of the fluid, and cause the effusion to be automatically absorbed, so that the effect of treatment is achieved. However, the parts where the substance acts is not targeted, the substance acts on the metabolic balance in the vitreous cavity, and the surgical method involves the intraocular vitreous body. Therefore, all interventions on the natural vitreous body of the human eye by surgery are irreversible, and this surgical method may cause great damage to the vitreous body of the patient.

SUMMARY

Accordingly, it is necessary to provide a foldable pressing balloon structure that reduces the incision during the surgery, does not stretch the extraocular muscles, and does not cause discomfort to the patient after surgery, and has simple operation, low difficulty, and short surgery time.

A foldable pressing balloon structure includes a balloon body configured to be provided in a fascia bulbi of an eyeball and a self-sealing drainage component. The balloon body has a balloon cavity configured to be filled with normal saline or air. The balloon body has a first surface having flat shape and a second surface having a curved shape. A height of the balloon body along the first surface is in a range from 0.2 cm to 2.0 cm. The drainage component is connected to the second surface of the balloon body and in communication with the balloon cavity.

In an embodiment, one of surfaces of the drainage component is flush with the first surface.

In an embodiment, the drainage component includes a drainage tube and a drainage valve, and the drainage valve is connected to the balloon body and in communication with the balloon cavity through the drainage tube.

In an embodiment, an outer surface of the drainage valve has a curved shape.

In an embodiment, the drainage valve has a columnar structure, and a radial dimension of the drainage valve is decreased gradually from an end of the drainage valve connected to the drainage tube to the opposite end of the drainage valve.

In an embodiment, a maximum radial dimension of the drainage valve is in a range from 0.1 cm to 1.0 cm, and a minimum radial dimension is in a range from 0.1 cm to 1.0 cm.

In an embodiment, a diameter of the drainage tube is smaller than the minimum radial dimension of the drainage valve.

In an embodiment, the foldable pressing balloon structure further includes a fixing body, the fixing body is connected to the second surface of the balloon body, and a tail end of the fixing body facing outward has a rounded shape.

In an embodiment, the number of the fixing bodies is at least two.

In an embodiment, at least a pair of the fixing bodies are arranged in opposite positions.

The foldable pressing balloon structure of the present disclosure has the following beneficial effects:

(1) In the foldable pressing balloon structure of the present disclosure, the balloon body has the first surface having a flat shape and the second surface having a curved shape, and the height of the balloon body along the first surface is in a range from 0.2 cm to 2.0 cm, which is more suitable for implantation under the fascia bulbi, and there is no need to be implanted into the vitreous cavity as in the conventional technique. Implanting the balloon body under the fascia bulbi of the eyeball is intended to act as a soft pressing object, so that under an external force, the detached retina is attached to the detached part, and then by cooperating with laser or condensation, the hole is sealed, thereby achieving the effect of treatment.

(2) The filling inside the balloon cavity is different from the conventional technology. In the conventional technology, the filling material is silicone oil. A diameter of the silicone oil molecule is larger than that of the pores in the surface of the balloon, such that the silicone oil may not leak out and may be permanently stored in an eye. The filling material inside the balloon cavity of the present disclosure is normal saline or air. Diameters of the water molecule and the gas molecule are smaller than that of the pores in the surface of the balloon, such that normal saline or air may gradually leak out, and the pressing action of the balloon at the implantation position may be gradually reduced as the patient recovers after surgery. When the patient heals after the surgery, the balloon is punctured to release the filling medium inside, or the balloon is removed directly.

(3) The drainage valve has a columnar structure, and the radial dimension of the drainage valve gradually decreases from an end of the drainage valve connected to the drainage tube to the opposite end of the drainage valve, and the drainage valve is designed as a circular truncated structure, which effectively reduces the volume of the drainage valve and is more suitable for balloon implantation under the fascia bulbi.

(4) In the present disclosure, fixing bodies are provided on both sides of the balloon body. The function of the fixing bodies is to fix the balloon body, prevent the balloon body from being displaced, improve the stability of the foldable pressing balloon structure, and improve the treatment effect.

(5) In the present disclosure, the balloon body is implanted under the fascia bulbi of the eyeball, and filling the medium inside the balloon body to press and seal the hole. Compared with the scleral encircling band in the conventional technology, there is no need for the encircling band fixing in the present disclosure, and it only needs to sew and fix the position of the drainage component to prevent displacement, such that the incision during the surgery is reduced, and since no encircling band fixing is required, the extraocular muscle is not stretched, and the patient has no discomfort after the surgery. In addition, the surgery time is greatly shortened due to the simple operation and reduced difficulty of the surgery. Further, since the surgery method of the foldable pressing balloon structure of the present disclosure does not involve the operation in the vitreous cavity during implantation, it does not interfere with the natural vitreous of the human body, and the original natural vitreous of the human eye of the patient is preserved.

10: foldable pressing balloon structure; 100: balloon body; 110: first surface; 120: second surface; 200: drainage component; 210: drainage valve; 220: drainage tube; 300: fixing body.

DETAILED DESCRIPTION OF THE EMBODIMENTS

In order to facilitate the understanding of the present disclosure, the present disclosure will be described more fully hereinafter with reference to the related accompanying drawings. Preferred embodiments of the present disclosure are shown in the accompanying drawings. However, the present disclosure may be embodied in many different forms and is not limited to the embodiments described herein. Rather, these embodiments are provided such that a thorough and complete understanding of the present disclosure is provided.

It should be noted that when an element is referred to as being "fixed to" another element, it can be directly fixed to the other element or an intervening element may also be present. When an element is considered to be "connected to" another element, it can be directly connected to another element or an intervening element may also be present. When an element is considered to be "mounted on" another element, it may be directly mounted on the other element or an intervening element may also be present. When an element is considered to be "disposed on" another element, it can be directly disposed on the other element or an intervening element may also be present.

All technical and scientific terms used herein have the same meaning as commonly understood by skilled person in the art to which the present disclosure belongs, unless otherwise defined. The terms used herein in the description of the present disclosure are for the purpose of describing specific embodiments only, and are not intended to limit the present disclosure. As used herein, the term "and/or" includes any and all combinations of one or more of the associated listed items.

Figure 1:
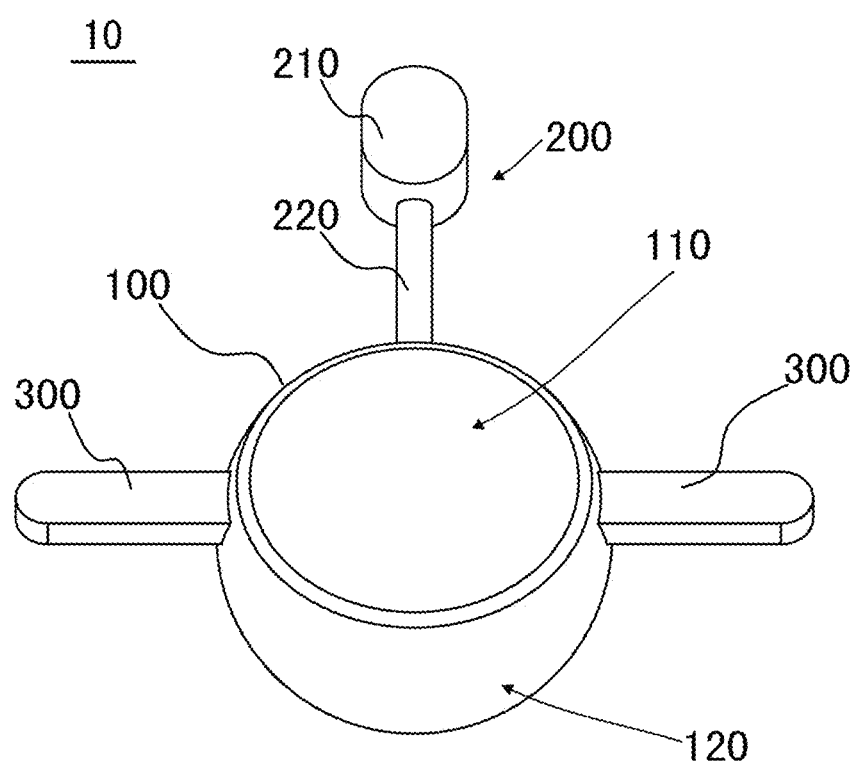
FIG. 1 is a schematic structural view illustrating a foldable pressing balloon according to an embodiment of the present disclosure.
Figure 2:
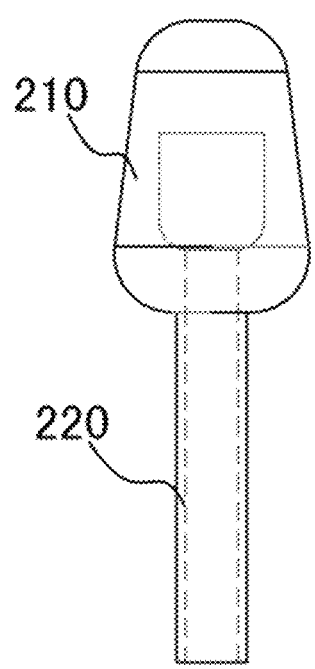
FIG. 2 is a schematic view illustrating a drainage component of the foldable pressing balloon structure shown in FIG. 1.

Referring to FIG. 1, an embodiment of the present disclosure provides a foldable pressing balloon structure 10, which includes a balloon body 100 configured to be provided in a fascia bulbi of an eyeball and a self-sealing drainage component 200.

Figure 4:
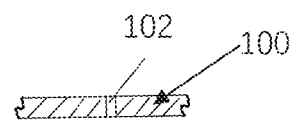
FIG. 4 is a schematic view illustrating a portion of the surface of the balloon body of the foldable pressing balloon structure shown in FIG. 1.

The balloon body 100 has a balloon cavity configured to be filled with saline or air. The filling inside the balloon cavity is different from the conventional technology. In the conventional technology, the filling material is silicone oil. A diameter of the silicone oil molecule is larger than that of pores in a surface of the balloon, such that the silicone oil may not leak out and may be permanently stored in the eye. The filling material inside the balloon cavity of the present disclosure is normal saline or air. Diameters of the water molecule and the gas molecule are smaller than that of pores 102 (see FIG. 4) in the surface of the balloon body 100, such that normal saline or air may gradually leak out, and the pressing action of the balloon at the implantation position may be gradually reduced as the patient recovers after surgery. When the patient heals after the surgery, the balloon is punctured to release the filling medium inside, or the balloon is removed directly.

The balloon body 100 has a first surface 110 having a flat shape and a second surface 120 having a curved shape. A height of the balloon body 100 along the first surface 110 is in a range 0.2 cm to 2.0 cm, and the drainage member 200 is fixedly connected to the second surface 120 of the balloon body 100 and in communication with the balloon cavity. In the foldable pressing balloon structure 10 of the present disclosure, the balloon body 100 has the first surface 110 having a flat shape and the second surface 120 having a curved shape, and the height of the balloon body 100 along the first surface 110 is in a range from 0.2 cm to 2.0 cm, which is more suitable for implantation under the fascia bulbi, and there is no need to be implanted into the vitreous cavity as in the conventional technique. implanting the balloon body 100 under the fascia bulbi of the eyeball is intended to act as a soft pressing object, so that under an external force is configured, the detached retina is attached to the detached part, and then by cooperating with laser or condensation, the hole is sealed, thereby achieving the effect of treatment.

Figure 3:
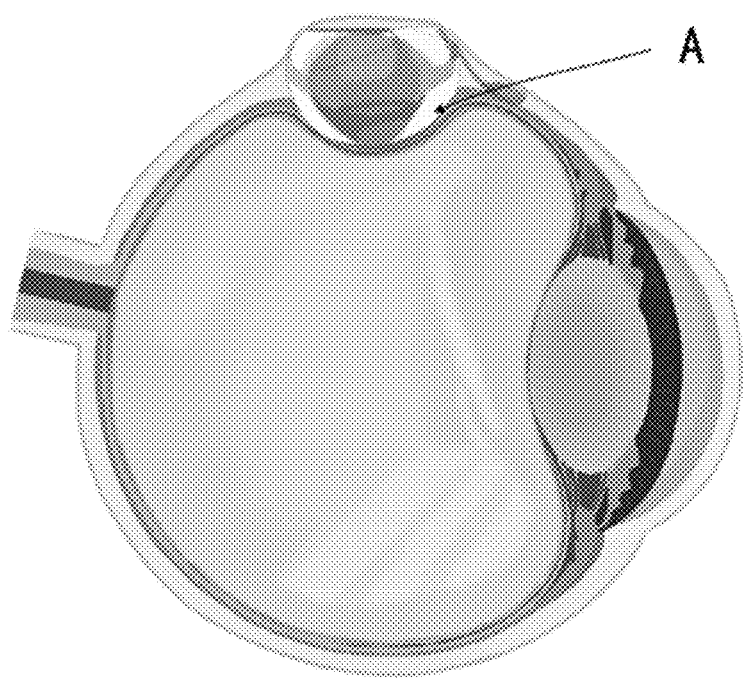
FIG. 3 is a schematic view illustrating a mounting position of the foldable pressing balloon structure shown in FIG. 1.

Preferably, the second surface 120 has a spherical shape, such that the balloon body 100 has a spherical crown structure. The balloon body 100 with the spherical crown structure is adapted to the position under the fascia bulbi of the eyeball to the greatest extent, as shown in FIG. 3, thereby reducing the foreign body sensation in the eye.

Further, one of surfaces of the drainage component 200 is flush with the first surface 110.

Further, the drainage component 200 includes a drainage tube 220 and a drainage valve 210, and the drainage valve 210 is connected to the balloon body 100 and in communication with the balloon cavity through the drainage tube 220.

Preferably, an outer surface of the drainage valve 210 has a curved shape.

In another embodiment, the drainage valve 210 has a columnar structure, preferably a cylindrical structure, and a radial dimension of the drainage valve 210 is decreased gradually from an end of the drainage valve 210 connected to the drainage tube 220 to the opposite end of the drainage valve 210. The drainage valve 210 has a columnar structure, and the radial dimension of the drainage valve 210 gradually decreases from an end of the drainage valve 210 connected to the drainage tube 220 to the opposite end of the drainage valve 210, and the drainage valve 210 is designed as a circular truncated structure, which effectively reduces the volume of the drainage valve 210 and is more suitable for balloon implantation under the fascia bulbi.

Further, a maximum radial dimension of the drainage valve 210 is in a range from 0.1 cm to 1.0 cm, and a minimum radial dimension is in a range from 0.1 cm to 1.0 cm.

Further, a diameter of the drainage tube 220 is smaller than a minimum radial dimension of the drainage valve 210.

In another embodiment, the foldable pressing balloon structure 10 of the present disclosure further includes a fixing body 300. The fixing body 300 is mounted on the second surface 120 of the balloon body 100. In the present disclosure, fixing bodies 300 are provided on both sides of the balloon body 100. The function of the fixing bodies 300 is to fix the balloon body 100, prevent the balloon body 100 from being displaced, improve the stability of the foldable pressing balloon structure 10, and improve the treatment effect.

Preferably, the number of the fixing bodies 300 is at least two. At least a pair of the fixing bodies 300 are arranged in opposite positions. Referring to FIG. 1, the number of the fixed bodies 300 is shown as two, and it is not difficult to understand that in other embodiments, the number of the fixing bodies 300 may also be other numbers, such as three or four or the like.

Further, the fixing body 300 has a shape of a long strip, and the tail end of the fixing body 300 facing outward has a rounded shape. The rounded end is capable of reducing the foreign body sensation of the fixing body 300 after being implanted into the eyeball, and improve the treatment effect.

In the present disclosure, the balloon body 100 is implanted under the fascia bulbi of the eyeball, and filling the medium inside the balloon body 100 to press and seal the hole. Compared with the scleral encircling band in the conventional technology, there is no need for a encircling band fixing in the present disclosure, and it only needs to sew and fix the position of the drainage component 200 to prevent displacement, such that the incision during the surgery is reduced, and since no encircling band fixing is required, the extraocular muscle is not stretched, and the patient has no discomfort after the surgery. Besides, the time required for the surgery is shortened due to the simple operation and reduced difficulty of the surgery. Further, since the surgery method of the foldable pressing balloon structure 10 of the present disclosure does not involve the surgery in the vitreous cavity during implantation, it does not interfere with the natural vitreous of the human body, and the original natural vitreous of the human eye of the patient is preserved.

The foldable pressing balloon of the aforementioned embodiment is configured to be implanted under the fascia bulbi of the eyeball, and is applied in the rhegmatogenous retinal detachment external-route surgery. This surgery has been successfully carried out in many cases, and the treatment effect of rhegmatogenous retinal detachment has been achieved after surgery, which proves that the new application of the foldable pressing balloon of the present disclosure for treating rhegmatogenous retinal detachment is effective.

The technical features of the aforementioned embodiments may be combined arbitrarily. To simplify the description, not all the possible combinations of the technical features in the aforementioned embodiments are described. However, all of the combinations of these technical features should be considered as within the scope of the present disclosure, as long as such combinations do not contradict with each other.

The aforementioned embodiments are merely illustrative of several examples of the present invention, and the description thereof is very specific and detailed, but is not to be construed as limiting the scope of the present invention. It should be noted that a plurality of variations and modifications may be made by those skilled in the art without departing from the scope of the present disclosure, which are all within the scope of protection of the present disclosure. Therefore, the protection scope of this invention shall be defined by the appended claims.

What is claimed is:

1. A foldable pressing balloon structure, comprising a balloon body configured to be provided in a fascia bulbi of an eyeball for an external-route surgery for rhegmatogenous retinal detachment, a self-sealing drainage component, and at least two fixing bodies, wherein the balloon body has a balloon cavity configured to be filled with normal saline or air, the balloon body has a first outer surface having a shape of a flat surface and a second outer surface having a curved shape, the drainage component extend outwardly from the second outer surface of the balloon body without covering the first outer surface and in communication with the balloon cavity, and the at least two fixing bodies are spaced from each other and extend outwardly from the second outer surface of the balloon body, and a tail end of each of the at least two fixing bodies facing outward has a rounded shape.

2. The foldable pressing balloon structure of claim 1, wherein one of surfaces of the drainage component is flush with the first surface.

3. The foldable pressing balloon structure of claim 1, wherein the drainage component comprises a drainage tube and a drainage valve, and the drainage valve is connected to the balloon body and in communication with the balloon cavity through the drainage tube.

4. The foldable pressing balloon structure of claim 3, wherein an outer surface of the drainage valve has a curved shape.

5. The foldable pressing balloon structure of claim 4, wherein the drainage valve has a columnar structure, and a radial dimension of the drainage valve is decreased gradually from an end of the drainage valve connected to the drainage tube to an opposite end of the drainage valve.

6. The foldable pressing balloon structure of claim 5, wherein a maximum radial dimension of the drainage valve is in a range from 0.1 cm to 1.0 cm, and a minimum radial dimension is in a range from 0.1 cm to 1.0 cm.

7. The foldable pressing balloon structure of claim 3, wherein a diameter of the drainage tube is smaller than a minimum radial dimension of the drainage valve.

8. The foldable pressing balloon structure of claim 1, wherein at least a pair of the fixing bodies are arranged in opposite positions.

9. The foldable pressing balloon structure of claim 1, wherein the balloon body comprises pores such that the normal saline or the air is capable of gradually leaking out of the balloon cavity via the pores.

10. The foldable pressing balloon structure of claim 1, wherein each of the fixing bodies has an elongated shape with two ends in a length direction thereof, one of the two ends is connected to the second outer surface of the balloon body directly, and another one of the two ends extends outwardly from said one of the two ends in the length direction.

11. The foldable pressing balloon structure of claim 3, wherein the drainage tube extends outwardly from the second outer surface of the balloon body without passing through the first outer surface.

12. The foldable pressing balloon structure of claim 11, wherein the first outer surface has a round periphery, and the drainage tube and the fixing bodies are distributed around the second outer surface of the balloon body in a circumferential direction of the second outer surface in a radial pattern.

* * * * *